United States Patent [19]

Pratt et al.

[11] 4,438,769

[45] Mar. 27, 1984

[54] MEDICAL STAPLE DEVICE

[76] Inventors: Clyde R. Pratt, 5898 La Cumbre, Somis, Calif. 93066; Roger G. Carignan, 219 Mara Ave., Ventura, Calif. 93004

[21] Appl. No.: 368,621

[22] Filed: Apr. 15, 1982

[51] Int. Cl.³ .............................................. A61B 17/18
[52] U.S. Cl. ............................ 128/334 R; 128/92 EC
[58] Field of Search .......... 128/334 R, 334 C, 92 EC, 128/92 B, 337

[56] References Cited

U.S. PATENT DOCUMENTS 3,208,450  9/1965  Abelson ......................... 128/92 EC
4,263,903  4/1981  Griggs ............................ 128/334 R Primary Examiner—John D. Yasko
Attorney, Agent, or Firm—Cislo, O'Reilly & Thomas

[57] ABSTRACT

A medical staple device for holding, driving, and withdrawing medical staples comprising a uniquely configured integral member of metal construction wherein, due to the intrinsic nature of the material, opposed staple holding portions are formed which naturally tend to move away from each other and wherein the terminii of the opposed portions are configured to receive in secure, captive relationship therebetween a medical staple which is to be held, driven or withdrawn from bone, tissue and the like. A sleeve or driver member is threadably associated with the device to exert, in a discrete manner, closing forces upon the opposed portions retaining the medical staple to either secure it therebetween or to release same from its grasp. The device is of relatively low-cost, unsophisticated construction and essentially trouble-free in operation.

16 Claims, 6 Drawing Figures

MEDICAL STAPLE DEVICE

BACKGROUND OF THE INVENTION

The prior art, as exemplified by U.S. Pat. No. 4,263,903 to Griggs, issued Apr. 28, 1981 and directed to MEDICAL STAPLE MEANS, teaches and discloses a medical device for use with medical staples. In the medical area it becomes highly desirable to be able to attach soft tissue and even artificial ligaments to bone structure such as would be necessary in repairing sports related injuries, fractures, torn ligaments and such occurrences.

The prior art, especially that as afore-cited, employs a device which is somewhat cumbersome to use, relatively expensive to manufacture, and having a plurality of components that will not always insure the maintenance-free operation of the device.

The herein disclosed invention is directed to a relatively unsophisticated, inexpensive and easy-to-use medical staple device which has the versatility which allows its use under a variety of conditions and needs.

OBJECTS AND SUMMARY OF THE INVENTION

It is an object of the invention to provide a medical staple device for holding, driving and withdrawing medical staples.

It is another even further object of the invention to provide a medical staple device of simplified construction and wherein the device is essentially trouble-free in operation.

It is another even more further specific object of the invention to provide a medical staple device for use in holding, driving and withdrawing medical staples wherein the device is easy to use and relatively easy to manufacture and fabricate.

It is another even more further, still more specific object of the invention to provide a medical staple device having the ability to be used under a wide variety of conditions and needs.

It is another even more specific and further important object of the invention to provide an integrally constructed staple retaining member having integral spaced and opposed portions made from metal wherein the spaced portions are naturally urged away from each other.

It is another even further, more important and more specific object of the invention to provide a staple device wherein an integral piece of turned bar stock is machined and cut so as to provide opposed staple holding portions which are naturally and normally biased away from each other.

It is another even further, more specific and illustrative object of the invention to provide a staple device for use with medical staples wherein a staple retaining member has integral spaced and opposed portions which are normally and inherently urged away from each other and which are adapted to receive and retain a medical staple therebetween wherein the opposed portions have abutment surfaces and an abutment means exerts selective, discrete forces to retain or release the medical staple from grip between the spaced and opposed portions.

It is another even further, even more illustrative and exemplary object of the invention to provide a medical staple device which has a variety and versatility of uses wherein extending sections may be associated with the device and wherein a slide hammer is utilized to deliver driving forces by which to drive staples, being retained by the staple device, through soft tissue and into bone and the like.

In an exemplary embodiment, the device of the invention pertains to one for holding, driving and withdrawing medical staples comprising the combination of an integrally constructed staple retaining member having integral, spaced and opposed portions normally and inherently urged away from each other and being adapted to receive and retain the medical staple therebetween. The integral, spaced and opposed portions have force application surfaces to which force may be applied to overcome the normal and inherent urging away force to releasably retain a medical staple therebetween. A force-applying and force-reduction member is cooperatively associated with the integrally constructed staple retaining member for selective application or removal of discrete forces upon said force application surfaces.

These and further objects of the invention will become more apparent from the hereinafter following commentary taken in conjunction with the drawings.

DESCRIPTION OF THE BEST EMBODIMENTS CONTEMPLATED

Figures 5, 6:
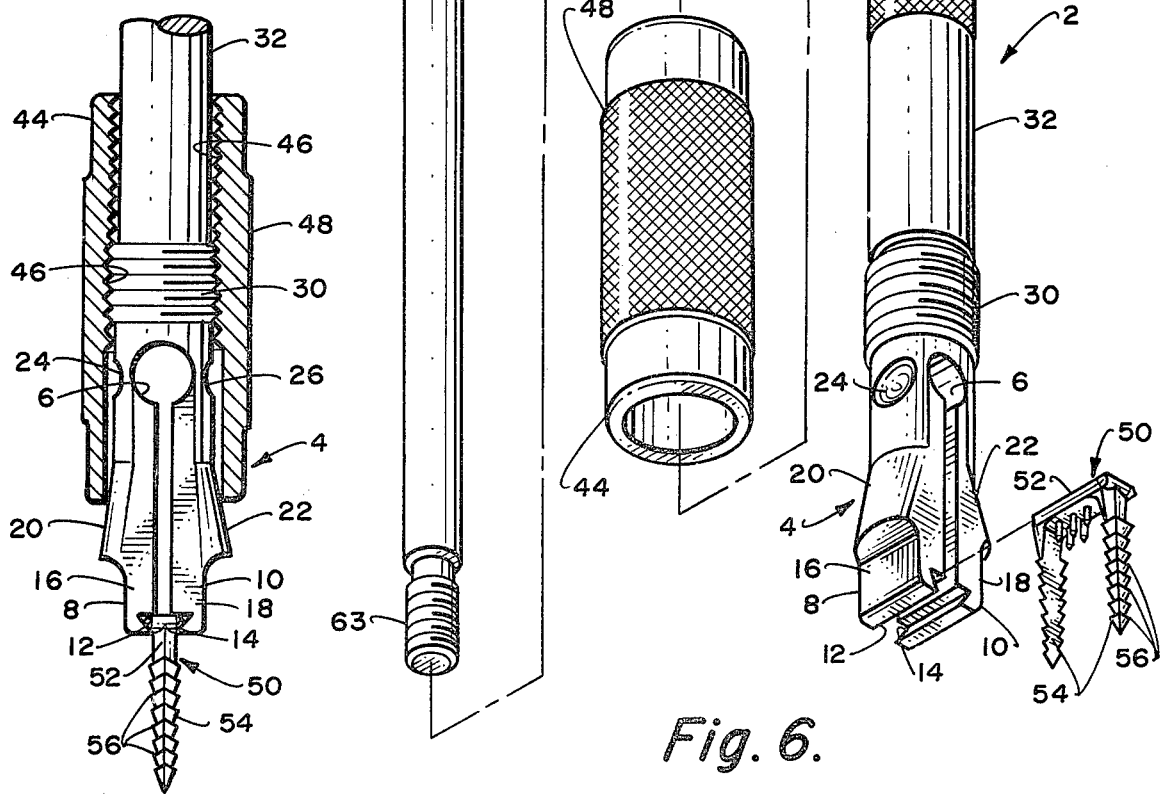
FIG. 5 is a view similar to that shown in FIG. 4 but showing the driver, nut or sleeve in the loosening mode.
FIG. 6 illustrates the components making up the devices of the invention in exploded form.

Referring to the figures of drawing where like numerals of reference designate like elements throughout, the basic unit or component of the device 2 comprises the structure best seen in FIG. 6. In the basic unit of the inventive medical staple holder 2 the device comprises an integrally constructed staple retaining member 4, in this particular instance, 17-4PM stainless steel turned bar stock formed in a manner such that a drilled-through bore 6 along with slot-cutting of the portion 4 produces opposed and spaced apart portions 8 and 10 having an interior configuration 12 and 14 respectively, to receive and accommodate the head or crossbar of a medical staple as will become apparent.

The staple retaining member portion 4 has a notched configuration as at 16 and 18 so as to permit better viewing of the work area which is to be worked upon with the device 2 of the invention. The opposed, spaced apart staple retaining portions 8 and 10 are naturally and intrinsically sprung outward from each other so that the tendency of each of the portions is to move away from one another. In that posture and position the medical staple, and more particularly the head and crossbar thereof, may be easily associated with the interior sections as, for example, 12–14 configured to receive a particular medical staple having a particular configuration. The specifics of the configuration will be delved into hereinafter.

Upward and adjacent to the notched portions 16 and 18 are force application or inclined surfaces 20 and 22 against which forces may be applied in order to either compress or release opposed staple retaining portions 8 and 10 as will become apparent.

Adjacent the bore 6 are opposed notches 24 and 26 which serves to reduce the cross-section of the staple retaining portion 4 so that proper spring action is imparted to the opposed staple retaining sections 8 and 10. To that end the bore 6 acts likewise to provide proper spring tension to the extending and depending opposed portions 8 and 10.

The exterior surface of the extending portion 30 of the device 2 is threaded with the remainder of the extending portions 32 terminating in the terminus 34 having threaded bore 36 adapated to receive striker nut or endcap 38 in threaded relationship therewith. The exterior surface of portion 32 as at 40, may be knurled as the surface 42 of end cap or nut 38 for ease of grasping and manipulation.

In the device 2 thus far described, best seen in FIG. 6, the remaining component necessary to obtain actuation of device 2 is driver, nut or sleeve 44 of cylindrical configuration and having a larger diameter than the diameter of the device 2. An interior portion 46 of sleeve 44 is threaded so that same may be associated in a cooperative manner with the threads 30 of device 2. The exterior surface of sleeve 44 may also be knurled as at 48.

When the sleeve 44 is associated with the threads 30 of device 2, the device 2 is then ready to have the device prepared to receive a medical staple, as for example, 50, in this particular instance having a unique diamond-shaped crossbar 52 with triangular depending legs 54, in this particular instance having barbs 56 thereon for ease of retention in the bone and tissue.

The interior surfaces 12 and 14 are accordingly, congruently-shaped to accommodate the diamond crossbar configuration of crossbar 52 of medical staple 50. Obviously, the interior surfaces 12 and 14 may be otherwise shaped to receive medical staples, or the like, having crossbars of different configuration, it only being important that congruency be observed so that the medical staple will be firmly grasped between the opposed portions 8 and 10 in the manner contemplated by the invention.

Figure 4:
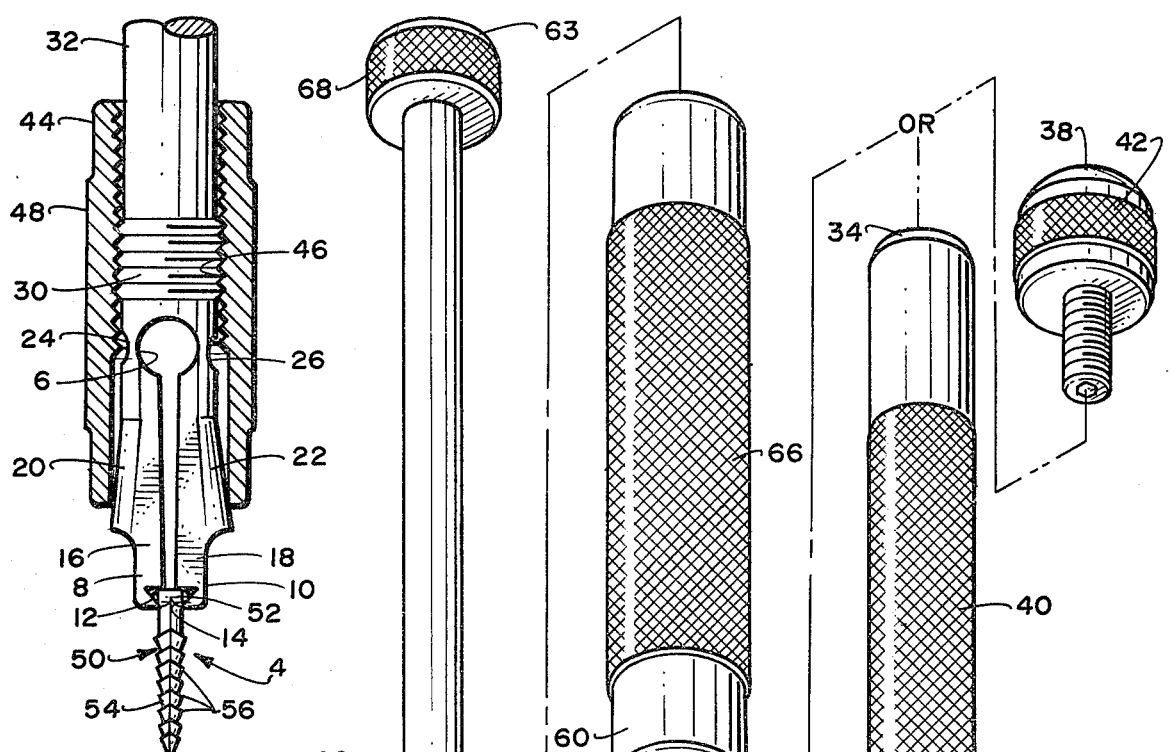
FIG. 4 is an enlarged fragmented view taken along the line 4—4 from FIG. 3.

In the FIG. 6 embodiment, the driver, nut or sleeve 44 is associated with the device 2 and threadably engaged on the threads 30 to about the position seen in FIG. 5. The end cap or nut 38 may then be threadably secured to the terminus 34. In this position, the device 2 is now ready to receive a staple 50. It will be noted that the driver, nut or sleeve 44 is linearly moveable in an axial direction with the device 2 and downward movement, as best in FIG. 5, urges the opposed staple retaining portions 8 and 10 closer and closer together as the sleeve advances so that eventually the sleeve reaches the position best seen in FIG. 4 to securely and rigidly retain medical staple 50 so that the staple may now be driven into position either by using a hammer to tap on the end of striker nut 38 and thereby drive the staple through soft tissue and into the bone for secure retention, or as will become apparent, the alternative expedient of the invention.

Figure 1:
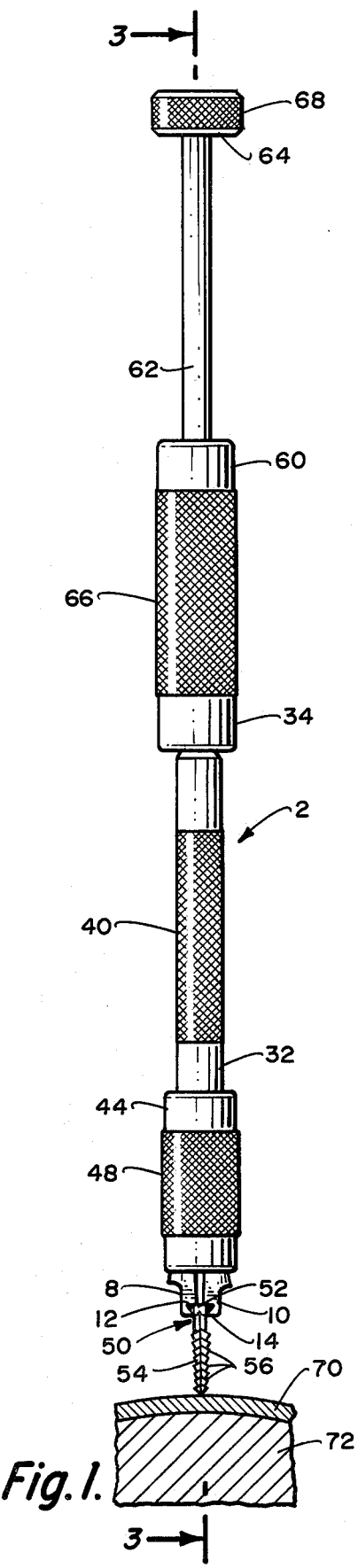
FIG. 1 is a side elevational view of one of the embodiments of the invention illustrating the device of the invention retaining a medical staple just prior for insertion thereof in a medical manner.

The alternative of the invention contemplates, in addition to the device 2, an extender and slide hammer which will now be described. In this embodiment, the end striker nut 38 is removed, and after the driver, nut or sleeve 44 is positioned on the portion 32, a slide hammer weight 60 of sufficient diameter to receive slide hammer shaft 62 having threaded end 63 and end nut or cap portion 64 is provided. The end 63 of slide hammer shaft 62 is threaded into bore 36 thus completing the alternative assemblage, as best seen in FIG. 1. The exterior surface 66 of slide hammer weight 60 may be knurled as is the exterior surface 68 of end nut or cap 64 for purposes already alluded to.

Referring to FIG. 1 the assembled device 2 has been positioned over soft tissue 70 and underlying bone 72. The device 2 with its associated medical staple 50 is now ready for operation. In this instance, instead of applying a linear or impacting force on the end of nut 38, the slide hammer weight member 60 is used to impart linear forces at the terminus 34 which is slightly larger in diameter than the interior bore of slide hammer weight member 60 so that movement thereof in a linear fashion, from about the terminus 34 up to the end cap or nut 64, permits application of driving force to drive the medical staple through the soft tissue 70 and into the underlying bone 72, best seen in FIGS. 1 and 2.

Figure 2:
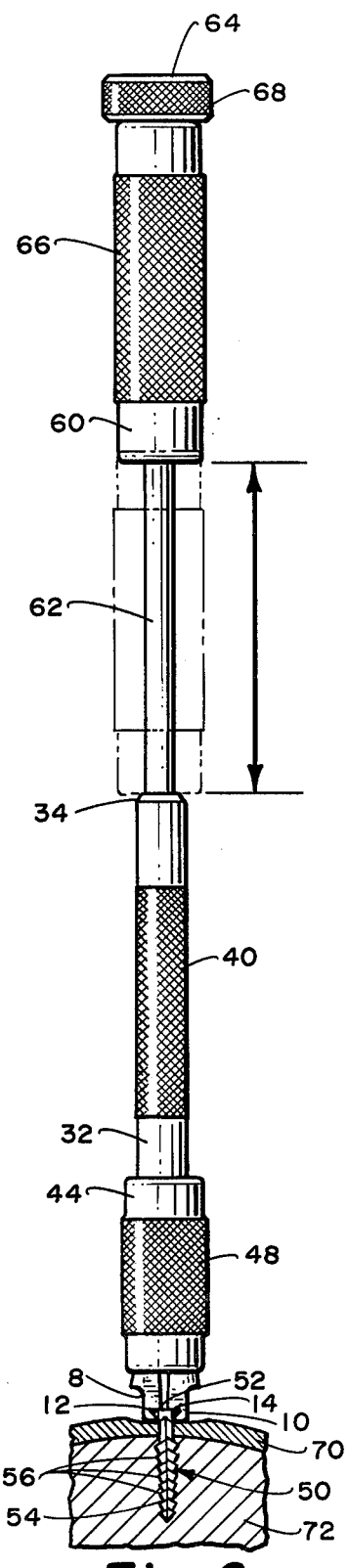
FIG. 2 is a view similar to FIG. 1 showing the medical staple inserted and illustrating the manner in which a slide hammer is utilized in which to impart linear forces to drive the staple through soft tissue and bone.
Figure 3:
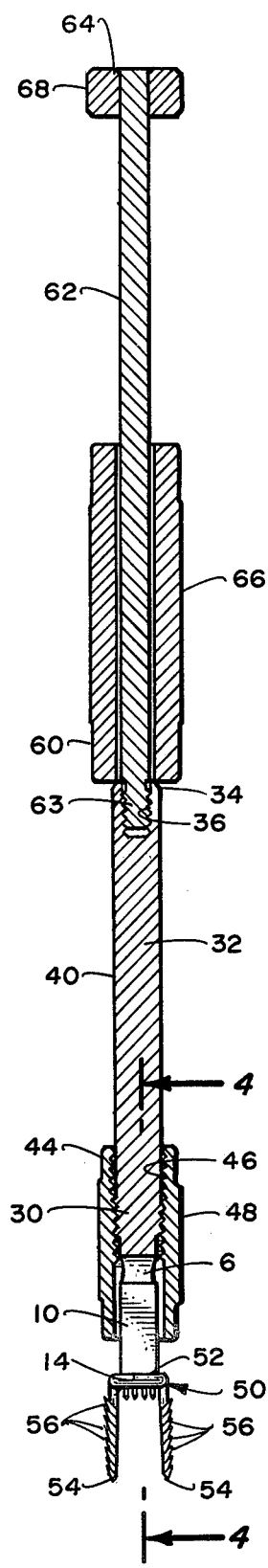
FIG. 3 is a view taken along the line 3—3 of FIG. 1 with the soft tissue and bone removed for purposes of clarity.

In FIG. 1 the device 2 is illustrated in the position prepared for insertion of the staple and in this instance the extended embodiment is utilized, which extended embodiment permits the versatility of use of the device of the invention with regard to hard to get at places and the like. Upon positioning of the device 2 (FIG. 1) the slide hammer weight member 60 is raised to the extreme limit of movement, which limit is caused by end nut or cap 64. The slide hammer weight 60 may be allowed to fall by itself to the phantom line (FIG. 2) to thereby apply linear forces at the terminus 34 to drive the staple 50 through the soft tissue 70 and into the bone 72, as best seen in FIG. 2. In the FIG. 2 showing, the arrow illustrates the extent through which the slide hammer member 60 may be raised. Obviously, the member 60 may be raised the entire length of the arrow distance or any part thereof. Additionally, the member 60 may be allowed to fall freely, or in some instances, applied forces may be exerted by way of the knurled surface 68 having additional force or pressure exerted by the operating surgeon's hand or hands.

There has thus been disclosed a medical staple device for holding, positioning and driving medical staples. The device may be used in the short or the lengthened form depending upon circumstances dictated by the procedure contemplated to be performed. Obviously, where staples are desired to be removed, the staple holder 2 is positioned so as to grasp the head of the staple and thereafter a dislodging force applied to withdraw the inserted medical staple from friction retention with bone, soft tissue and the like.

While the invention has been described with respect to particular materials of construction and specific configured components, it should be observed that the device of the invention, having the unitary nature of construction that the basic unit has, is less costly to fabricate, has fewer number of parts thereby making for essentially trouble-free operation, and further is versatile to the extent of permitting hammer-applied forces or forces applied by means of the slide hammer weight associated with the extending slide hammer shaft.

Those of ordinary skill in the art will at once recognize various changes and modifications and all such changes and modifications are intended to be covered by the appended claims.

We claim:

1. A medical staple device for holding, driving and withdrawing same comprising the combination: an integrally constructed staple retaining member having integral, spaced and opposed portions normally and inherently urged away from each other and being adapted to receive and retain a medical staple therebetween, said integral, spaced and opposed portions having force application surfaces to which force may be applied to overcome the normal and inherent urging away force to releasably retain a medical staple therebetween; and a force applying and force reduction member cooperatively associated with said integrally constructed staple retaining member for selective application or removal of discrete forces upon said force application surfaces.

2. The medical staple device in accordance with claim 1 wherein said integrally constructed staple retaining member is of metal wherein the intrinsic spring characteristic thereof causes said spaced and opposed portions to be normally urged away from each other.

3. The medical staple device in accordance with claim 2 wherein said staple retaining member is constructed of turned bar stock.

4. The medical staple device in accordance with claim 2 wherein the terminii of said spaced and opposed portions are congruently configured to at least the upper portion of the medical staple with which they are adapted to be associated with.

5. The medical staple device in accordance with claim 4 wherein said force application surfaces are inclined surfaces adapted to be abutted by said force applying and force reduction member.

6. The medical staple device in accordance with claim 5 wherein a portion of the exterior surface of said integrally constructed staple retaining member is provided with threads.

7. The medical staple device in accordance with claim 6 wherein said force applying and force reduction member is a sleeve having a threaded interior portion for threaded coaction, in a linear manner, with the threaded portion of said integrally constructed staple retaining member.

8. The medical staple device in accordance with claim 7 wherein associated movement of said sleeve either towards or away from said abutting surfaces either urges toward or biases away said spaced, opposed portions.

9. The medical staple device in accordance with claim 8 including an extending portion extending from said spaced and opposed portions for manipulating said staple retaining member.

10. The medical staple device in accordance with claim 9 wherein said extending portion is adapted to have linear forces applied to the end thereof.

11. The medical staple device in accordance with claim 10 wherein said end of said extending portion is adapted to releaseably receive a slide hammer shaft.

12. The medical staple device in accordance with claim 11 including a slide hammer member adapted to be captively retained on said slide hammer shaft and linearly move along the extent thereof.

13. The medical staple device in accordance with claim 12 wherein the end of said extending portion extends beyond the diameter of said slide hammer and is adapted to receive linearly applied forces from said slide hammer.

14. The medical staple device in accordance with claim 13 wherein the end of said extending portion is provided with a threaded bore and one end of said slide hammer shaft is threaded for association therewith and the other end is provided with a cap having a larger diameter than said slide hammer member.

15. The medical staple device in accordance with claim 14 wherein said staple retaining member is annular in configuration and the portion of said staple retaining member adjacent said force application surfaces is of reduced diameter.

16. A medical staple holder and driver comprising the combination: an elongate, integrally constructed staple retaining member, one end having integral, spaced apart and naturally sprung opposed portions having interior wall surfaces adapted to coincide with and retain a like configured medical staple therebetween when said opposed portions are urged towards each other, said opposed positions being resilient and normally tending to assume the spaced apart, sprung condition and the upper portions thereof having outwardly flaring surfaces; and a driver sleeve member in encompassing, cooperative relationship to said staple retaining member and being adapted to abut said outwardly flaring surfaces to permit closing or opening forces thereon to either urge or permit movement of said opposed portions towards or away from each other, the terminus of said other end of said staple retaining member being adapted to have linear forces applied thereto.

* * * * *